United States Patent [19]
White

[11] Patent Number: 5,431,916
[45] Date of Patent: Jul. 11, 1995

[54] PHARMACEUTICAL COMPOSITIONS AND PROCESS OF MANUFACTURE THEREOF

[75] Inventor: Richard K. White, Maineville, Ohio

[73] Assignee: The Procter & Gamble Company, Cincinnati, Ohio

[21] Appl. No.: 54,762

[22] Filed: Apr. 29, 1993

[51] Int. Cl.$^6$ .............................................. A61K 9/48
[52] U.S. Cl. .................... 424/451; 424/452; 424/455; 424/456; 514/772.3; 514/785
[58] Field of Search .............. 424/451, 452, 455, 443, 424/445, 456

[56] References Cited

U.S. PATENT DOCUMENTS

| | | | |
|---|---|---|---|
| 3,632,547 | 1/1972 | Kajioka | 424/443 |
| 3,784,684 | 1/1974 | Bossert et al. | 424/37 |
| 3,851,051 | 11/1974 | Miskel et al. | 424/37 |
| 4,067,960 | 1/1978 | Fadda | 424/14 |
| 4,198,391 | 4/1980 | Grainger | 424/37 |
| 4,690,823 | 9/1987 | Lohner et al. | 424/456 |
| 4,727,109 | 2/1988 | Schmidt et al. | 424/455 |
| 4,744,988 | 5/1988 | Brox | 424/456 |
| 4,764,378 | 8/1988 | Keith et al. | 424/435 |
| 4,780,316 | 10/1988 | Brox | 424/456 |
| 4,820,522 | 4/1989 | Radebaugh et al. | 424/468 |
| 4,857,312 | 8/1989 | Hegasy et al. | 424/80 |
| 4,888,239 | 12/1989 | Brox | 428/402.2 |
| 4,968,509 | 11/1990 | Radebaugh et al. | 424/470 |
| 5,006,595 | 4/1991 | Smith et al. | 524/548 |
| 5,071,643 | 12/1991 | Yu et al. | 514/570 |
| 5,141,961 | 8/1992 | Coapman | 514/629 |

FOREIGN PATENT DOCUMENTS

| | | | |
|---|---|---|---|
| 0152292 | 8/1985 | European Pat. Off. | A61K 9/48 |
| 2185887 | 8/1987 | United Kingdom | A61K 31/55 |

OTHER PUBLICATIONS

"Citrate Esters", Morflex, Inc. Technical Bulletin 101.
"Specialized Drug Delivery Systems", Drugs & The Pharmaceutical Sciences, vol. 41, ed. P. Tyle.
M. S. Patel, F. S. S. Morton & H. Seager, "Advances in softgel formulation technology", Manufaturing Chemist, Jul. 1989.
N. H. Shah, D. Stiel, M. H. Infeld, A. S. Railkar, A. W. Malick & M. Patrawala, "Elasticity of Soft Gelatin Capsules Containing Polyethylene Glycol 400–Quantitation and Resolution", Pharmaceutical Technology, Mar. 1992.
M. S. Patel, F. S. S. Morton, H. Seager & D. Howard, "Factors Affecting the Chemical Stability of Carboxylic Acid Drugs in Enhanced Solubility System (ESS) Softgel Formulations based on Polyethylene Glycol (PEG)", Drug Development and Industrial Pharmacy, 18(1), 1–19 (1992).

*Primary Examiner*—Thurman K. Page
*Assistant Examiner*—James M. Spear
*Attorney, Agent, or Firm*—David K. Dabbiere; Douglas C. Mohl; Jacobus C. Rasser

[57] ABSTRACT

The present invention describes a product comprising least one pharmaceutically acceptable active in a mixture of a tri-ester and polyvinylpyrrolidone, and a process for producing the same. In further embodiments, the present invention also relates to a process for encapsulating the composition within soft gelatin shells. The resulting compositions and capsules provide an effective means for oral delivery of a wide variety of pharmaceutically acceptable actives.

19 Claims, No Drawings

PHARMACEUTICAL COMPOSITIONS AND PROCESS OF MANUFACTURE THEREOF

TECHNICAL FIELD

The present invention relates to pharmaceutical compositions comprising at least one pharmaceutically acceptable active in a mixture of a tri-ester and polyvinylpyrrolidone, and a process for manufacturing such pharmaceutical compositions. Further embodiments relate to a process for encapsulating such pharmaceutical compositions within a soft gelatin shell. The resulting compositions and capsules provide an effective means for oral delivery of a wide variety of pharmaceutically acceptable actives.

BACKGROUND OF THE INVENTION

Soft gelatin capsules, commonly referred to as softgels and seamless soft gelatin capsules, are each one piece capsules containing pharmaceutically acceptable actives or other compounds in a liquid or semi-liquid state. These capsules are fashioned, filled and sealed in one continuous operation. Soft gelatin capsules containing liquid pharmaceutical compositions provide an excellent system for the delivery of pharmaceutically acceptable actives. Soft gelatin capsules are a preferred dosage form for accurately dispensing liquids, offering a simple means of masking the unpleasant taste and aromas of many pharmaceutically acceptable actives. Soft gelatin capsules are also convenient, portable and easy to swallow.

Upon ingestion into the gastrointestinal tract the gelatin capsule ruptures releasing its contents. Unlike solids, softgels which contain a liquid do not first have to disintegrate prior to exhibiting a pharmacological action.

Soft gelatin capsules provide accurate and uniform delivery of a unit dose of a pharmaceutically acceptable active, an advantage which becomes especially important when delivering relatively small amounts of pharmaceutically acceptable actives. Soft gelatin capsules are also aesthetically appealing, especially when filled with a transparent liquid.

However, despite these advantages it is not always possible to prepare a liquid composition of the desired pharmaceutically acceptable active. Soft gelatin capsules are limited by the selection of solvents available for solubilizing and suspending pharmaceutically acceptable actives due to toxicity and capsule volume considerations.

Various methods have been employed to overcome this downfall. See U.S. Pat. No. 4,794,117, to Corbiere, issued Dec. 27, 1988; U.S. Pat. NO. 4,690,823, to Lohner et al., issued Sep. 1, 1987; U.S. Pat. No. 3,784,684, to Bossert et al., issued Jan. 8, 1974; PCT Application No. WO88/02625, to Yu et al., published Apr. 21, 1988; European Patent Application No. 152,292, to Rogers, published Aug. 21, 1985. U.S. Pat. No. 3,865,603, to Szymanski et al., issued Feb. 11, 1975; U.S. Pat. No. 2,580,683, to Kreuger, issued Jan. 1, 1952; Japanese Pat. No. 84044096, to Morishita, issued Jan. 26, 1984 and U.S. Pat. No. 5,141,961, to Coapman, issued Aug. 25, 1992.

The solvent system of the present invention has significant solvating properties able to dissolve relatively large quantities of pharmaceutically acceptable actives; producing concentrated solvent-active mixtures. Previous solvent systems utilized common solvents such as propylene glycol and polyethylene glycols; each providing excellent solvency but neither being completely appropriate for an important category of pharmaceutically acceptable active agents, the nonsteroidal anti-inflammatory compounds. Without being limited by theory, it is believed that many nonsteroidal anti-inflammatory compounds, like numerous other pharmaceutically acceptable actives, are strong acids which react with hydroxylated and poly-hydroxylated solvent and plasticizer species such as propylene glycol, polyethylene glycols and glycerin forming the pro-drug ester of the active compound. The present inventor has found tri-esters, when pared with polyvinylpyrrolidone creates an excellent solvent system for, but not limited to, nonsteroidal anti-inflammatory compounds and other acidic pharmaceutically acceptable actives, without the drawbacks of solvents containing reactive hydroxyl groups. Additionally, these tri-esterpolyvinylpyrrolidone systems allow for the facilitated selection of a plasticizer, by being nonsolvents for glycerin and possibly other plasticizers commonly used in soft gelatin capsule manufacturing. By being a nonsolvent, the tri-ester-polyvinylpyrrolidone system creates a barrier preventing the migration of the plasticizer from the soft gelatin shell into the pharmaceutically acceptable active/solvent fill.

Another advantage of the present tri-ester-polyvinylpyrrolidone solvent system is the tri-ester's water tolerance. This low water tolerance allows for the inclusion of additional water soluble pharmaceutically acceptable actives, expanding the range of activity of a single composition.

It is an object of the present invention to provide pharmaceutical compositions containing at least one pharmaceutically acceptable active in a mixture of a tri-ester and polyvinylpyrrolidone. Another object of the present invention is to provide a process for solubilizing or suspending at least one pharmaceutically acceptable active in a mixture of a tri-ester and polyvinylpyrrolidone. A further object of the present invention is to depict a process for preparing soft gelatin capsules containing a composition comprising at least one pharmaceutically acceptable active in a mixture of a tri-ester and polyvinylpyrrolidone; the soft gelatin shell being optionally transparent. A still further object of the present invention is to provide soft gelatin capsules containing at least one pharmaceutically acceptable active in a mixture of a tri-ester and polyvinylpyrrolidone, in which the soft gelatin shell is optionally transparent. These and other objects of this invention will become apparent in light of the following disclosure.

SUMMARY OF THE INVENTION

The present invention relates to pharmaceutical compositions comprising:
  (i) a safe and effective amount of a tri-ester; and
  (ii) a safe and effective amount of polyvinylpyrrolidone; in a ratio of from about 2.0 to about 0.5 to about 1.0 to about 1.0; and
  (iii) a safe and effective amount of at least one pharmaceutically acceptable active
  (iv) an orally acceptable carrier.

The present invention also relates to a process for preparing the above described composition and a process for preparing soft gelatin capsules containing pharmaceutical compositions of the above described invention.

All percentages and ratios used herein are by weight and all measurements are at 25° C., unless otherwise indicated.

The term "pharmaceutically acceptable active", as used herein, describes any chemical material or compound suitable for administration and having a pharmacological action.

The active materials or compounds useful in the present invention should be compatible with each other and the other components of the instant composition.

DETAILED DESCRIPTION OF THE INVENTION PHARMACEUTICAL COMPOSITIONS

The pharmaceutical compositions of the present invention comprise the following essential, as well as optional components.

Tri-esters

An essential component of the present compositions is a triester. Tri-esters are generally clear, viscous liquids with a bitter taste and low toxicity. Tri-esters of the present invention correspond to the general formula:

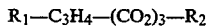

$$R_1-C_3H_4-(CO_2)_3-R_2$$

where $R_1$ is H—, HO—, or $CH_3COO$— and $R_2$ is an alkyl of between 1 and 4 carbons.

Tri-esters their effects and uses are described further by: "Citrate Esters", Morflex® Technical Bulletin 101; Publication No. EFC-214, May 1991, Eastman Kodak Company®; Bruns, F. H. u. Werners, H. P. (1962), Zum Stoffwechsel von Triathylcitrat und Acetyltrathylcitrat. Kln. Wschr. 40, 1169; Golaz, M., Guess, W. L. & Autian, J. (1967). Mechanistic toxicology of triethyl citrate in mouse fibroblast cells by liquid scintillation techniques. J. Pharm. Sci. 56, 1252; The Merck Index, Eleventh Edition, entry 2328, 9504, p. 362, 1510 (1989), herein incorporated by reference.

Tri-esters useful in the present invention are exemplified by triethyl citrate $C_3H_5O(COOC_2H_5)_3$; glyceryl triacetate $C_3H_5(OCOCH_3)_3$; acetyltriethyl citrate $CH_3COOC_3H_4(COOC_2H_5)_3$; and acetyltri-n-butyl citrate $CH_3COOC_3H_4(COOC_4H_9)$. The preferred tri-esters are triethyl citrate and glyceryl triacetate. Triethyl citrate, acetyltriethyl citrate and acetyltriethyl citrate can be obtained from Morflex®, Inc., Greensboro, N.C. 27403. Glyceryl triacetate can be obtained from Eastman Chemical Products, Inc., Kingsport, Tenn. 37662 under the name Triacetin®.

The pharmaceutical compositions of the present invention comprise from about 10% to about 50%, more preferably from about 20% to about 40%, and most preferably from about 30% to about 40% of a tri-ester selected from the group consisting of triethyl citrate, glyceryl triacetate, acetyltriethyl citrate, acetyltriethyl citrate and mixtures thereof.

Polyvinylprrolidone

Another essential component of the present invention is polyvinylpyrrolidone, which is a polymer of N-vinyl-2-pyrrolidone having the following formula:

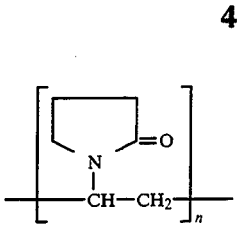

Polyvinylpyrrolidones are described in L. Blecher et al. in Handbook of Water-Soluble Gums & Resins, R. L. Davidson, Ed. (McGraw-Hill, New York, 1980) pp. 21/1-21/21, incorporated herein by reference. Polyvinylpyrrolidone has different solubility characteristics based on its polymeric structure. Long-chain polyvinylpyrrolidone, which is also known as povidone, has good solubility in water and a number of organic solvents. Cross-linked polyvinylpyrrolidone, which is also known as crospovidone, is insoluble in virtually all common solvents. Both the soluble and insoluble forms of polyvinylpyrrolidone are commercially available from International Specialty Products, P.O. Box 1006, Bound Brook, N.J., under the Plasdone® and Polyplasdone® trademarks, respectively, and from BASF Aktiengesellschaft, Ludwigshafen, Germany, under the Kollidon® trademark. Soluble forms of polyvinylpyrrolidone include Plasdone® K-25, Plasdone® K-26/28, Plasdone® K-29/32, Plasdone® C-15, Plasdone® C-30, Plasdone® C-90, Kollidon® 12 PF, Kollidon® 17 PF, Kollidon® 25, Kollidon® 30, and Kollidon® 90. Insoluble forms of polyvinylpyrrolidone include Polyplasdone XLR, Polyplasdone XLR10, Kollidon® CL, and Kollidon® CL-M. See "Tableting With Plasdone®", GAF Technical Bulletin 2302-110R1 (1986); "Polyplasdone XLR, Polyplasdone XLR10", GAF Technical Bulletin 2302-099 R2 (1984); and "Kollidon® Grades, Polyvinylpyrrolidone for the Pharmaceutical Industry", BASF Technical Bulletin MEF 129e, Register 2, May 1986 (Bn); incorporated herein by reference.

The soluble forms of polyvinylpyrrolidone are preferred for use in the present invention. Preferred are soluble polyvinylpyrrolidones having an average molecular weight in the range from about 2,900 to about 1,100,000; more preferred are those having an average molecular weight in the range from about 2,900 to about 45,000; and most preferred are those having an average molecular weight of about 2,900 to about 9,000. Moreover, mixtures of two or more soluble polyvinylpyrrolidones of different average molecular weight can be employed.

The pharmaceutical compositions of the present invention comprise from about 10% to about 50% of polyvinylpyrrolidone, more preferably from about 20% to about 40% and most preferably from about 25% to about 30%.

An important requirement of the pharmaceutical compositions of the present invention is that the tri-ester component and the polyvinylpyrrolidone component are present in a proper ratio. The ratio of the total amount of tri-ester to polyvinylpyrrolidone should be in a range from about 2.0 to about 0.5, to about 1.0 to about 1.0.

Without being restricted by theory, a perceived advantage of using a tri-ester and polyvinylpyrrolidone combination as a solubilization or suspending system, is the systems' lack of plasticizer miscibility. Glycerin and other polyol plasticizers have minimal solubility in the tri-ester-polyvinylpyrrolidone combination. Glycerin, and possibly other polyol plasticizers utilized in many soft gel capsules tends to migrate into the solvent-active fill, causing the capsule to become brittle and less malleable over time. This possibility may change the compositions bioavailability profile and may shorten shelf life. Furthermore, when utilizing pharmaceutically acceptable actives containing a carboxylic acid moiety, glycerin or another plasticizer having a reactive alcohol group, migrating from the gelatin shell would react with the carboxylic acid-active forming a pro-drug ester possibly altering the stability of the pharmaceutically acceptable active or composition. Similarly, adding glycerin or polyethlyene glycol to the fill to prevent migration is inappropriate with strong acid actives as a pro-drug ester is formed. However, the use of a tri-ester-polyvinylpyrrolidone solvent system precludes the need to add a plasticizer to the fill and allows for an improved use of the available pharmaceutically acceptable active fill volume.

Pharmaceutically Acceptable Actives

The compositions of the instant invention contain at least one pharmaceutically acceptable active as an essential component. Useful classes of pharmaceutically acceptable active compounds which can be incorporated into the present compositions include, but are not limited to, analgesics, anti-inflammatory agents, antipyretics, calcium channel blockers, beta-blockers, antibacterials, antidepressants, antidiabetics, anti-emetics, antihistamines, cerebral stimulants, sedatives, anti-parasitics, expectorants, diuretics, decongestants, antitussives, muscle relaxants, anti-Parkinsonian agents, bronchodilators, cardiotonics, antibiotics, antivirals, nutritional supplements (such as vitamins, minerals, fatty acids, amino acids, and the like), their pharmaceutically-acceptable salts and compatible mixtures thereof. Pharmaceutical acceptable actives selected from the nonnarcotic analgesics/nonsteroidal anti-inflammatory drugs are also useful in the present invention. Examples of such drugs are disclosed in U.S. Pat. No. 4,522,828, to Sunshine et al., issued Jun. 11, 1985; U.S. Pat. No. 4,619,934, to Sunshine et al., issued Oct. 28, 1986 and U.S. Pat. No. 4,783,465, to Sunshine et al., issued Nov. 8, 1988, all incorporated herein by reference.

The term "pharmaceutically acceptable salts" refers to salts prepared from pharmaceutically acceptable non-toxic bases including inorganic bases and organic bases. Salts derived from nonorganic bases include sodium, potassium, lithium, ammonia, calcium, magnesium, ferrous, zinc, manganous, aluminum, ferric, manganic salts and the like. Salts derived from pharmaceutically acceptable organic nontoxic bases include salts of primary, secondary, tertiary and quaternary amines, substituted amines including naturally occurring substituted amines, cyclic amines and basic ion exchange resins, such as triethylamine, tripropylamine, 2-dimethylaminoethanol, 2-diethylaminoethanol, lysine, arginine, histidine, caffeine, procaine, N-ethylpiperidine, hydrabamine, choline, betaine, ethylenediamine, glucosamine, methylglycamine, theobromine, purines, piperazine, piperidine, polyamine resins and the like.

Examples of preferred pharmaceutically acceptable actives useful in the present invention include, but are not limited to, acetaminophen, acetylsalicylic acid, ibuprofen, flurbiprofen, ketoprofen, naproxen, loperamide, their pharmaceutically-acceptable salts, and compatible mixtures thereof.

Further examples of pharmaceutically acceptable actives useful in the present invention include, but are not limited to, pseudoephedrine, dextromethorphan, doxylamine, chlorpheniramine, ephedrine, triprolidine, diphenhydramine, phenyltoxylamine, guaifenesin, phenylpropanolamine, caffeine, their pharmaceutically-acceptable salts, and compatible mixtures thereof.

The pharmaceutical compositions of the present instant invention comprise from about 0.01% to about 50% of a pharmaceutically acceptable active, more preferably from about 0.1% to about 40%, and most preferably from about 1% to about 30%.

Without being confined by theory, it is believed that pharmaceutically acceptable actives in a solvent system of the present invention exhibit a greater bioavailability and reach higher peak concentrations that other pharmaceutical formulations. Formulations of the present invention, although initially manifesting a depressed absorption rate due to the highly hydrophobic nature of the tri-ester, subsequently enjoy higher peak concentrations and exhibit a greater total area under a time-concentration curve. This greater area under the time-concentration curve conveys a greater total bioavailability for the composition.

Persons skilled in the art will immediately realize many other ingredients will be suitable for inclusion in the present invention. Nonessential components which can be incorporated into the compositions of the instant invention include, but are not limited to: additional solubilizing agents, colorings, surfactants, flavorings, preservatives, lubricants, flow-enhancers, viscosity modifiers, filling aids, anti-oxidants, essences, and other compounds, agents and components which produce an appealing final product.

Another nonessential component is a crystallization inhibitor or a precipitation inhibitor. Examples of compositions having a crystallization or precipitation inhibitor can be found in U.S. Pat. No. 4,940,701, issued to Davis, Jul. 10, 1990 and incorporated herein by reference.

An optional component that may be used to solubilize certain pharmaceutical actives is polyethylene glycol. Polyethylene glycols generally are clear, viscous liquids or white solids which are soluble in water and many organic solvents. These polymers correspond to the general formula:

$$H(OCH_2CH_2)_nOH$$

where n is greater than or equal to 4. Polyethylene glycols are described in G. M. Powell, III in *Handbook of Water-Soluble Gums & Resins*, R. L. Davidson, Ed. (McGraw-Hill, New York, 1980) pp. 18/1–18/31, this reference being incorporated herein by reference in its entirety. Polyethylene glycols, which are also known as "PEGs" or "polyoxyethylenes", are designated by both their average molecular weight range and their average "n" value as in the above designated formula. For example, polyethylene glycol 400, which is also known by the CTFA designation, PEG-B, has an average molecular weight range from 380–420 and an average value of n between 8.2 and 9.1. See *CTFA Cosmetic Ingredient Dictionary*, Third Edition (1982), pp. 201–203; and *The Merck Index*, Tenth Edition, entry 7441, p. 1092 (1983), incorporated herein by reference.

The polyethylene glycols preferable herein are those which are liquids at room temperature or have a melting point slightly thereabove. Preferred are the polyethylene glycols having a molecular weight range from about 300 to about 4600 and corresponding n values from about 6 to about 104. More preferred are the polyethylene glycols having a molecular weight range from about 400 to about 3350 and corresponding n values from about 8 to about 76. Most preferred are the polyethylene glycols having a molecular weight range from about 600 to about 1000 and corresponding n values from about 12 to about 22. Most especially preferred is a polyethylene glycol having a molecular weight of about 600 and a corresponding n value of about 12. Moreover, mixtures of two or more polyethylene glycols of different average molecular weight range or n value can also be employed in the present invention. Liquid and low-melting polyethylene glycols are commercially available from Union Carbide (Danbury, Conn.) under the Carbowax ® trademark. See "Carbowax ® Polyethylene Glycols", Union Carbide Technical Bulletin f-4772M-ICD 11/86-20M, this reference being incorporated herein by reference in its entirety.

Depending on the pharmaceutically acceptable active, varying amounts of polyethylene glycol may be employed to facilitate dissolution of the pharmaceutically acceptable active. Polyethylene glycol is employed to facilitate the solubility of highly water soluble pharmaceutically acceptable actives that have modest to low solubility in the tri-ester component of the present invention. Alternatively, polyethylene glycol is used as a viscosity modifier allowing the suspension of fine particles of a pharmaceutically acceptable actives in suspension type formulations.

Another optional component that may be used to help solubilize certain pharmaceutical actives is an amount of water. Any water used in the present invention should preferably be deionized, distilled, free of organic impurities and bacteria and substantially free of metal ions.

Depending on the pharmaceutically acceptable active, varying amounts of water may be employed to facilitate dissolution of the pharmaceutically acceptable active in the tri-ester polyvinylpyrrolidone system. Water can be used alone or may be combined with other solvents primarily for highly water soluble pharmaceutically acceptable actives that have modest to low solubility in the tri-ester component of the present invention.

PROCESS AND MANUFACTURE OF PHARMACEUTICAL COMPOSITIONS

Pharmaceutical compositions of the present invention are combined using art-recognized principles and methodologies when intermixing ingredients and choosing the type of equipment to be used. In a preferred manner of manufacture, the tri-ester and polyvinylpyrrolidone are combined, heated and mixed until the polyvinylpyrrolidone is fully dissolved forming a homogeneous solution. Thereafter, the pharmaceutically acceptable active or actives are added. At this point, if a solution is desired, additional heat may be required to facilitate the dissolution of the pharmaceutically acceptable active. Optional components can either be added initially or after the essential components are combined. However, if polyethylene glycol, water, other additional solvents or a combination of solvents is being employed to facilitate the dissolution of the pharmaceutically acceptable active, the pharmaceutically acceptable active and water, polyethylene glycol, additional solvents or combination of solvents are admixed and then added to the tri-ester-polyvinylpyrrolidone combination. This addition is done, preferably at a reduced temperature to lessen the chances of thermal decomposition of any included pharmaceutically acceptable active.

After the final mixture has been formulated, if a solution, the mixture should be buffered as close to neutral as possible without precipitating the pharmaceutically acceptable active. If the final composition is to be a suspension, the formulation should be buffered to a pH of about 7. Buffering to approximately a neutral pH stabilizes the ester component of the invention reducing any tendency toward hydrolysis.

PROCESS AND MANUFACTURE OF SOFT GELATIN CAPSULES

Preselected amounts of the pharmaceutical compositions of the present invention can also be encapsulated within soft gelatin shells. Optionally, the soft gelatin shells are essentially transparent so as to enhance the aesthetic qualities of the capsule. The soft gelatin shells comprise the following essential, as well as optional, components.

Gelatin

Gelatin is an essential component of the soft gelatin shells of the instant invention. The starting gelatin material used in the manufacture of soft capsules is obtained by the partial hydrolysis of collagenous material, such as the skin, white connective tissues, or bones of animals. Gelatin material can be classified as Type A gelatin, which is obtained from the acid-processing of porcine skins and exhibits an isoelectric point between pH 7 and pH 9; and Type B gelatin, which is obtained from the alkaline-processing of bone and animal (bovine) skins and exhibits an isoelectric point between pH 4.7 and pH 5.2. Blends of Type A and Type B gelatins can be used to obtain a gelatin with the requisite viscosity and bloom strength characteristics for capsule manufacture. Gelatin suitable for capsule manufacture is commercially available from the Sanofi Bio-Industries, Waukesna, Wis. For a general description of gelatin and gelatin-based capsules, see *Remingtons Pharmaceutical Sciences*, 16th ed., Merck Publishing Company, Easton, Pa. (1980), page 1245 and pages 1576–1582; and U.S. Pat. No. 4,935,243, to Borkan et al., issued Jun. 19, 1990, incorporated herein by reference.

The soft gelatin shell of the capsules of the present invention, as initially prepared, comprises from about 20% to about 60% gelatin, more preferably from about 25% to about 50% gelatin, and most preferably from about 40% to about 50% gelatin. The gelatin can be of Type A, Type B, or a mixture thereof with bloom numbers ranging from about 60 to about 300.

Plasticizer

A plasticizer is another essential component of the soft gelatin shells of the instant invention. One or more plasticizer is incorporated to produce a soft gelatin shell. The soft gelatin thus obtained has the required flexibility characteristics for use as an encapsulation agent. Useful plasticizer of the present invention include glycerin, sorbitan, sorbitol, or similar low molecular weight polyols, and mixtures thereof.

The shell of the present invention, as initially prepared, comprises from about 10% to about 35% plasticizer. A preferred plasticizer useful in the present invention is glycerin.

Water

The soft gelatin shells of the instant invention also comprise water as an essential component. Without being limited by theory, the water is believed to aid in the rapid dissolution or rupture of the soft gelatin shell upon contact with the gastrointestinal fluids encountered in the body.

The shell of the present invention, as initially prepared, comprises from about 15% to about 50% water, more preferably from about 25% to about 40% water, and most preferably from about 30% to about 40% water.

Optional components which can be incorporated into the soft gelatin shells include colorings, flavorings, preservatives, antioxidants, essences, and other aesthetically pleasing components.

The pharmaceutical compositions of the present invention can be encapsulated within any conventional soft gelatin shell that is capable of substantially containing the composition for a reasonable period of time. The soft gelatin shells of the instant invention can be prepared by combining appropriate amounts of gelatin, water, plasticizer, and any optional components in a suitable vessel and agitating and/or stirring while heating to about 65° C. until a uniform solution is obtained; followed by deaeration. This soft gelatin shell preparation can then be used for encapsulating the desired quantity of the solubilized fill composition employing standard encapsulation methodology to produce one-piece, hermetically-sealed, soft gelatin capsules. The gelatin capsules are formed into the desired shape and size so that they can be readily swallowed. The soft gelatin capsules of the present invention are of a suitable size for easy swallowing and typically contain from about 100 mg to about 2000 mg of the solubilized pharmaceutical active composition. Soft gelatin capsules and encapsulation methods are described in P. K. Wilkinson et al., "Softgels: Manufacturing Considerations", *Drug and the Pharmaceutical Sciences*, 41 (Specialized Drug Delivery Systems), P. Tyle, Ed. (Marcel Dekker, Inc., New York, 1990) pp.409–449; F. S. Hom et al., "Capsules, Soft", *Encyclopedia of Pharmaceutical Technology*, vol. 2, J. Swarbrick and J. C. Boylan, eds. (Marcel Dekker, Inc., New York, 1990) pp. 269–284; M. S. Patel et al., "Advances in Softgel Formulation Technology", *Manufacturing Chemist*, vol. 60, no. 7, pp. 26–28 (July 1989); M. S. Patel et al., "Softgel Technology", *Manufacturing Chemist*, vol. 60, no. 8, pp. 47–49 (August 1989); R. F. Jimerson, "Softgel (Soft Gelatin Capsule) Update", *Drug Development and Industrial Pharmacy Interphex '86 Conference)*., vol. 12, no. 8 & 9, pp. 1133–1144 (1986) and W. R. Ebert, "Soft Elastic Gelatin Capsules: A Unique Dosage Form", *Pharmaceutical Technology*, vol. 1, no. 5, pp. 44–50 (1977) these references are incorporated by reference herein in their entirety. Alternatively, the pharmaceutical composition of the present invention can be encapsulated within a seamless soft gelatin shell. Seamless soft gelatin capsules and encapsulation methods are described by J. Rakucewicz, "Seamless Soft Gels . . . An Alternative to Contract Manufacturing", *Drug Development and Industrial Pharmacy*, vol. 14, no. 2 & 3, pp. 391–412 (1988), incorporated herein by reference. When manufacturing seamless soft gelatin capsules, it is the tri-ester of the present invention which produces the critical surface tension differential between the active fill and the gelatin shell necessary for the formation of the seamless soft gelatin capsule.

The resulting soft gelatin capsules are soluble in water and in gastrointestinal fluids. Upon swallowing the capsule, the gelatin shell rapidly dissolves or ruptures in the gastrointestinal tract thereby introducing the pharmaceutical actives into the physiological system.

METHOD OF MANUFACTURE

The pharmaceutical compositions of the present invention can be prepared using the methods described in the following examples.

EXAMPLES

The following examples further describe and demonstrate embodiments within the scope of the present invention. The examples are given solely for the purpose of illustration and are not to be construed as limitations or restrictions of the present invention, as persons skilled in the art will quickly realize, many variations thereof are possible without departing from the spirit and scope of the invention.

Example I

|  | W/W % |
| --- | --- |
| triethyl citrate[1] | 34.04 |
| polyvinylpyrrolidone 17 pf[2] | 34.04 |
| naproxen | 31.92 |

[1]Available as Citroflex ® 2, from Morflex ® , Greensboro, NC 27403.
[2]Available as Kollidon ® 17 pf, from BASF, Parsippany, NJ, 07054.

Polyvinylpyrrolidone is added to triethyl citrate in a suitable container, mixed and heated in a oil bath to 65–85 degrees Centigrade. Once the polyvinylpyrrolidone is dissolved, add naproxen with continued mixing maintaining 70–90 degrees Centigrade until all solids are completely dissolved. Deaerate this composition under vacuum while maintaining 60–80 degrees Centigrade. The resulting naproxen composition is suitable for oral administration, and encapsulation within soft gelatin shells.

Example II

Soft Gelatin Capsule Containing A Solubilized Naproxen Composition

A soft gelatin mixture is first prepared from the following ingredients.

|  | W/W % |
| --- | --- |
| Gelatin | 47.00 |
| Glycerin | 15.00 |
| Water | QS 100 |

The above ingredients are combined in a suitable vessel and heated with mixing at about 65° C. to form a uniform solution. Using standard encapsulation methodology, the resulting solution is used to prepare soft gelatin capsules containing approximately 187.5 mg of the naproxen composition of Example I. The resulting soft gelatin capsules are suitable for oral administration.

Example III

Solubilized Pharmaceutical Composition

|  | W/W % |
| --- | --- |
| triethyl citrate | 32.10 |
| polyvinylpyrrolidone 12 pf[1] | 24.08 |
| ibuprofen | 32.10 |
| pseudoephedrine HCl | 4.82 |
| water | 6.42 |

-continued

| | W/W % |
|---|---|
| ammonium hydroxide 30% | 0.48 |

[1] Available as Kollidon ® 12 pf, from BASF, Parsippany, NJ, 07054. The resulting composition is suitable for oral administration, and encapsulation within soft gelatin shells.

Example IV
Solubilized Pharmaceutical Composition

| | W/W % |
|---|---|
| glyceryl triacetate[1] | 25.21 |
| polyvinylpyrrolidone 12 pf | 25.21 |
| ibuprofen | 33.62 |
| pseudoephedrine HCl | 5.04 |
| diphenhydramine HCl | 4.20 |
| water | 5.04 |
| potassium hydroxide 42.5% | 1.68 |

[1] Available as Triacetin ®, from Eastman Fine Chemicals, Kingsport, TN, 37662. The resulting composition is suitable for oral administration, and encapsulation within soft gelatin shells.

Example V
Solubilized Pharmaceutical Composition

| | W/W % |
|---|---|
| triethyl citrate | 29.36 |
| polyvinylpyrrolidone 17 pf | 29.36 |
| ibuprofen | 29.36 |
| dextromethorphan HBr | 2.20 |
| doxylamine | 0.92 |
| pseudoephedrine HCl | 4.40 |
| water | 4.40 |

Examples III through V are manufactured using the methodology as explained in example I. The resulting composition is suitable for oral administration, and encapsulation within soft gelatin shells.

Example VI
Soft Gelatin Capsule Containing A Solubilized Pharmaceutical Composition.

A gelatin solution is prepared as described in Example II. Using standard encapsulation methodology, this gelatin solution is used to prepare soft gelatin capsules containing approximately 200 mg of the ibuprofen composition of Example V. The resulting soft gelatin pharmaceutical capsules are suitable for oral administration.

Example VII
Suspended Pharmaceutical Composition

| | W/W % |
|---|---|
| triethyl citrate | 32.30 |
| polyvinylpyrrolidone 12 pf | 19.38 |
| ibuprofen | 25.84 |
| caffeine | 13.30 |
| water | 6.46 |
| potassium hydroxide 45% | 0.52 |
| poloxamer 338[1] | 2.58 |

[1] Available as as Pluronic F108, from BASF Corp., Parsippany, NJ, 07054.

Polyvinylpyrrolidone and triethyl citrate are heated with mixing at approximately 65° C. To this mixture add ibuprofen water and potassium hydroxide with mixing. Caffeine is screened through 80 mesh and then added to the mixture. Melt poloxamer 338 and add with mixing. The resulting composition is suitable for oral administration, and encapsulation within soft gelatin shells.

Example VIII
Suspended Pharmaceutical Composition

| | W/W % |
|---|---|
| triethyl citrate | 22.86 |
| polyvinylpyrrolidone 17 pf | 17.14 |
| acetaminophen | 57.14 |
| polyethylene glycol 3350[1] | 2.86 |

[1] Available as Carbowax 3350, from Union Carbide, Danbury, CT, 06817.

Polyvinylpyrrolidone and triethyl citrate are heated with mixing at approximately 65° C. Polyethylene glycol 3350 is added and melted into solution. Acetaminophen is screened through 80 mesh and then added to the solvent blend and heated to 125° C. This produces a supersaturated solution of acetaminophen with the majority of drug remaining in a suspended form. The resulting composition is suitable for oral administration, and encapsulation within soft gelatin shells.

Example IX
Soft Gelatin Capsule Containing A Suspended Acetaminophen Composition A soft gelatin mixture is first prepared from the following ingredients.

| | W/W % |
|---|---|
| gelatin | 47.00 |
| glycerin | 12.00 |
| sorbitol | 14.00 |
| water | qs 100 |

A gelatin solution is prepared as described in Example II. Using standard encapsulation methodology, this gelatin solution is used to prepare soft gelatin capsules containing approximately 500 mg of the acetaminophen composition of Example VIII. The resulting soft gelatin acetaminophen capsules are suitable for oral administration.

What is claimed is:

1. A pharmaceutical encapsulated composition comprising:
   (i) a safe and effective amount of a tri-ester:
   (ii) a safe and effective amount of polyvinylpyrrolidone;
   (iii) a safe and effective amount of at least one pharmaceutically acceptable active selected from the group consisting of analgesics, anti-inflammatory agents, anti-pyretics, calcium channel blockers, beta-blockers, antibacterials, antidepressants, anti-diabetics, anti-emetics, antihistamines, cerebral stimulants, sedatives, anti-parasitics, expectorants, diuretics, decongestants, antitussives, muscle relaxants, anti-Parkinsonian agents, bronchodilators, cardiotonics, antibiotics, antivirals, nutritional supplements, their pharmaceutically-acceptable salts and compatible mixtures thereof; and
   (iv) an orally acceptable carrier
wherein the ratio of tri-ester to polyvinylpyrrolidone is from about 2.0 to about 0.5, to about 1.0 to about 1.0.

2. A pharmaceutical composition according to claim 1 which comprises from about 10% to about 50% of the tri-ester and is selected from the group consisting of triethyl citrate, glyceryl triacetate, acetyltriethyl citrate, acetyltri-n-butyl citrate and mixtures thereof.

3. A pharmaceutical composition according to claim 2 which comprises from about 10% to about 50% of the polyvinylpyrrolidone and has an average molecular weight of about 2,900 to about 1,100,000.

4. A pharmaceutical composition according to claim 3 which comprises from about 0.01% to about 50% of the pharmaceutically acceptable active, and is selected from the group consisting of an antitussive; an antinauseant; a nutritional supplement; a laxative; an appetite suppressant; an analgesic; an antiasthmatic; an antihistamine; a decongestant; a xanthine; an expectorant; an antacid; an antidiarrheal, a H2-Receptor antagonist and mixtures thereof.

5. A pharmaceutical composition according to claim 4 wherein the pharmaceutically acceptable active is an analgesic selected from the group consisting of acetaminophen, acetylsalicylic acid, ketoprofen, fenoprofen, flurbiprofen, ibuprofen, naproxen, and mixtures thereof.

6. A pharmaceutical composition according to claim which additionally contains from about 0.1% to about 20% water or polyethylene glycol and mixtures thereof.

7. A pharmaceutical composition according to claim 1 which additionally contains from about 0.1% to about 10% of a surfactant.

8. A pharmaceutical composition according to claim 4 which further contains a second pharmaceutically acceptable active selected from the group consisting of an antitussive; an antinauseant; a nutritional supplement; a laxative; an appetite suppressant; an analgesic; an antiasthmatic; an antihistamine; a decongestant; a xanthine; an expectorant; an antacid; an antidiarrheal; a H2-Receptor antagonist and mixtures thereof.

9. A pharmaceutical composition according to claim 8 which further contains a third pharmaceutically acceptable active selected from the group consisting of an antitussive; an antinauseant; a nutritional supplement; a laxative; an appetite suppressant; an analgesic; an antiasthmatic; an antihistamine; a decongestant; a xanthine; an expectorant; an antacid; an antidiarrheal; a H2-Receptor antagonist and mixtures thereof.

10. A pharmaceutical composition according to claim 9 which further contains a fourth pharmaceutically acceptable active selected from the group consisting of an antitussive; an antinauseant; a nutritional supplement; a laxative; an appetite suppressant; an analgesic; an antiasthmatic; an antihistamine; a decongestant; a xanthine; an expectorant; an antacid; an antidiarrheal; a H2-Receptor antagonist and mixtures thereof.

11. A composition according to claim 10 wherein the pharmaceutically acceptable actives are acetaminophen, dextromethorphan, pseudoephedrine and doxylamine or chlorpheniramine.

12. A pharmaceutical composition according to claim 1 encapsulated within a gelatin shell.

13. A process for preparing soft gelatin capsules containing a pharmaceutical composition comprising the steps of:
  (a) combining, mixing and heating a first component comprising:
    (i) a safe and effective amount of a tri-ester;
    (ii) a safe and effective amount of polyvinylpyrrolidone;
    (iii) a safe and effective amount of at least one pharmaceutically acceptable active; wherein the ratio of tri-ester to polyvinylpyrrolidone is from about 2.0 to about 0.5, to about 1.0 to about 1.0;
  (b) combining and admixing with component (a) a second component comprising:
    (i) from about 0.01% to about 50% of at least one pharmaceutically acceptable active; and
  (c) encapsulating the composition formed by admixing component (a) and component (b) within a soft gelatin shell.

14. A process according to claim 13 wherein the pharmaceutically acceptable active is selected from the group consisting of an antitussive; an antinauseant; a nutritional supplement; a laxative; an appetite suppressant; an analgesic; an antiasthmatic; an antihistamine; a xanthine; a decongestant; an expectorant; an antacid; an antidiarrheal, a H2-Receptor antagonist and mixtures thereof.

15. A process according to claim 13 which additionally contains from about 0.1% to about 20% of water or polyethylene glycol and mixtures thereof.

16. A process according to claim 13 which additionally requires heat when combining component (b).

17. A process according to claim 13 which additionally contains from about 0.1% to about 10.0% of a surfactant.

18. A method of providing relief of cold symptoms by administering a safe and effective amount of a composition produced according to claim 13.

19. A method of providing relief of cold symptoms by administering a safe and effective amount of a composition of claim 1.

* * * * *